US008429952B1

(12) United States Patent
Bringhurst et al.

(10) Patent No.: US 8,429,952 B1
(45) Date of Patent: Apr. 30, 2013

(54) SENSOR WITH ANTIFOULING CONTROL

(75) Inventors: Boyd T. Bringhurst, Logan, UT (US);
Craig B. Christensen, Logan, UT (US);
Daniel W. Ewert, Logan, UT (US); **R.
Joseph Thurston**, Logan, UT (US);
John P. Downing, Jr., Port Townsend,
WA (US)

(73) Assignee: Campbell Scientific, Inc., Logan, UT (US)

( * ) Notice: Subject to any disclaimer, the term of this patent is extended or adjusted under 35 U.S.C. 154(b) by 397 days.

(21) Appl. No.: 12/698,669

(22) Filed: Feb. 2, 2010

(51) Int. Cl.
*G01N 11/00* (2006.01)

(52) U.S. Cl.
USPC ............................................. 73/53.01

(58) Field of Classification Search .................. None
See application file for complete search history.

(56) References Cited

U.S. PATENT DOCUMENTS

| | | | | |
|---|---|---|---|---|
| 3,867,630 | A | * | 2/1975 | Urban ........................ 250/239 |
| 4,665,760 | A | * | 5/1987 | Eramo et al. ................ 73/866.5 |
| 4,763,537 | A | | 8/1988 | Scott et al. |
| 4,794,804 | A | * | 1/1989 | Ishii ........................... 73/865.6 |
| 6,111,249 | A | | 8/2000 | Garner, III |
| 6,142,297 | A | * | 11/2000 | Price .......................... 206/212 |
| 6,779,383 | B2 | | 8/2004 | Lizotte et al. |
| 6,842,243 | B2 | | 1/2005 | Tokhtuev et al. |
| 6,858,658 | B2 | | 2/2005 | Tomasgaard et al. |
| 7,040,157 | B2 | * | 5/2006 | Glasgow et al. ............ 73/170.29 |
| 7,106,437 | B2 | * | 9/2006 | Marrow et al. ............... 356/301 |
| 7,154,599 | B2 | * | 12/2006 | Adams et al. ................ 356/317 |
| 7,341,695 | B1 | | 3/2008 | Garner |
| 2007/0221510 | A1 | * | 9/2007 | Russell et al. ............. 205/789.5 |
| 2008/0006083 | A1 | * | 1/2008 | Feinstein et al. ............. 73/105 |
| 2009/0041621 | A1 | | 2/2009 | Kelly et al. |

FOREIGN PATENT DOCUMENTS

CN         1500568          2/2004

OTHER PUBLICATIONS

Alliance for Coastal Technologies Workshop Proceedings; "Biofouling Prevention Technologies for Coastal Sensors/Sensor Platforms", Solomons, MD, Nov. 19-21, 2003.
Alliance for Coastal Technologies Performance Verification Statement for the In-Situ Troll 9500 Turbidity Probe; UMCES Technical Report Series: Ref. No. [UMCES]CBL 07-051; Mar. 2007.
Alliance for Coastal Technologies Performance Verification Statement for the McVan Analite NEP395 Turbidity Probe; UMCES Technical Report Series: Ref. No. [UMCES]CBL 07-051; Mar. 2007.

* cited by examiner

*Primary Examiner* — Robert R Raevis
(74) *Attorney, Agent, or Firm* — Workman Nydegger

(57) ABSTRACT

A probe with antifouling components. The probe includes a sensor for measuring attributes of a fluid such as liquid or gas. The probe includes antifouling components to prevent or inhibit fouling. The antifouling components include material components, antifoulant components such as biocide, scaling inhibitors, etc., and wiper/shutter components that are arranged to collectively prevent or inhibit fouling of the probe or of the sensor included in the probe.

35 Claims, 9 Drawing Sheets

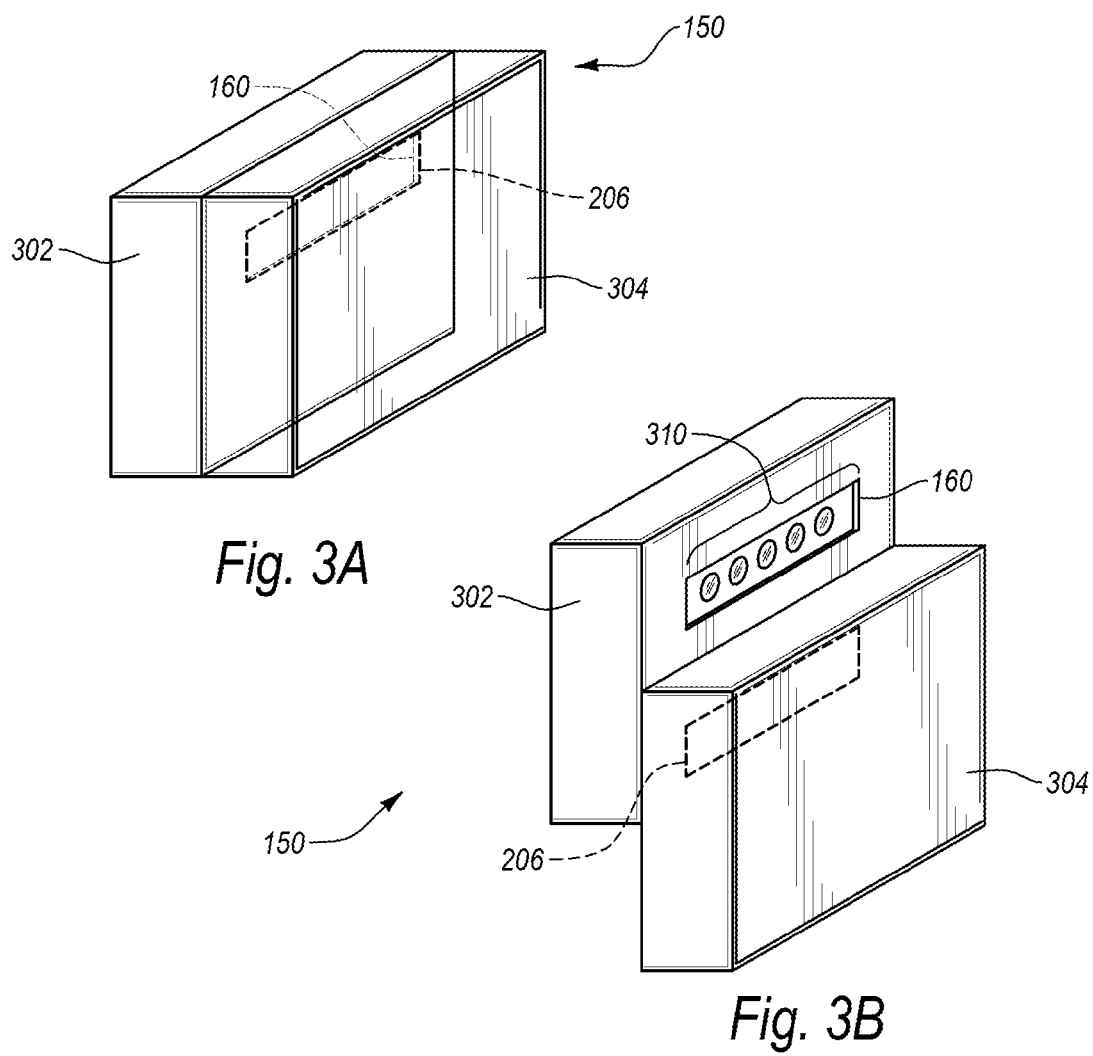
Fig. 3A
Fig. 3B
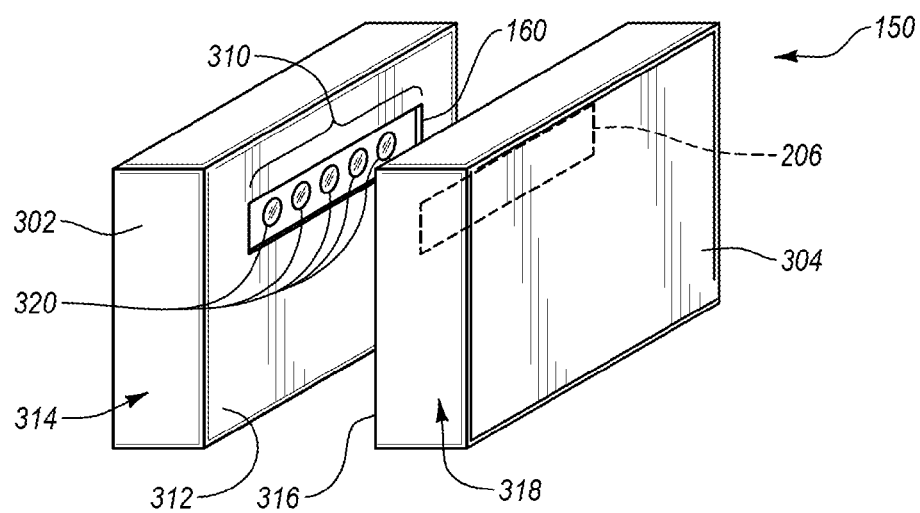
Fig. 4

SENSOR WITH ANTIFOULING CONTROL

BACKGROUND OF THE INVENTION

Water is a limited resource and is often managed or analyzed for at least environmental, economic, and health reasons. In fact, the water quality of oceans, rivers, reservoirs, and other bodies of water has an impact not only on the environment but also on the ability to use these resources effectively and efficiently. The quality of the water may also impact the cost associated with water management or water analysis.

The quality of water can be affected by many factors. The quality of water can be affected, for instance, when nutrients and salts are naturally added to the water from the environment. At the same time, the quality of water can also be affected from other activities such as sewage discharge, agriculture, mining, land development, dredging, or the like.

The quality of water is often determined by measuring characteristics or attributes of the water. Turbidity, pH, dissolved oxygen, temperature, and conductivity are commonly measured indicators of water quality. Each of these indicators provides certain information.

Turbidity, for example, is a measurement of the opaqueness of water. As the amount of suspended materials in the water increases, the water becomes murkier or less clear. In many bodies of water, for example, turbidity often increases after rainfall and flooding due in part to soil erosion.

The suspended materials impact the quality of the water in various ways. They may absorb nutrients or heavy metals and cause sedimentation, for example. Unless remedied, water having high turbidity can lead to health problems.

As with turbidity, high or low levels of pH, dissolved oxygen, temperature and conductivity can have adverse effects on wildlife, fish populations, human health, and esthetics. Unfortunately the cost of remediating water quality problems can be expensive.

Thus, measurements of water quality become tools that aid the analysis of water quality. Measuring the attributes or characteristics of water like turbidity of water is often performed using sensors. Unfortunately, sensors are subject to fouling (e.g., algae growth, mineral deposits, etc.). Fouling can increase the cost of water management because fouling can interfere with the operation of the sensor over time. As a result, it is necessary to either perform maintenance on the sensors or replace them with new sensors. In either case, the cost associated with measuring water quality is adversely affected.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3A illustrates a view of a probe in a closed position;

FIG. 3B illustrates a view of the probe in an open position;

FIG. 4 illustrates a perspective view of the probe that is separated into constituent portions;

DETAILED DESCRIPTION OF THE PREFERRED EMBODIMENTS

Figure 1:
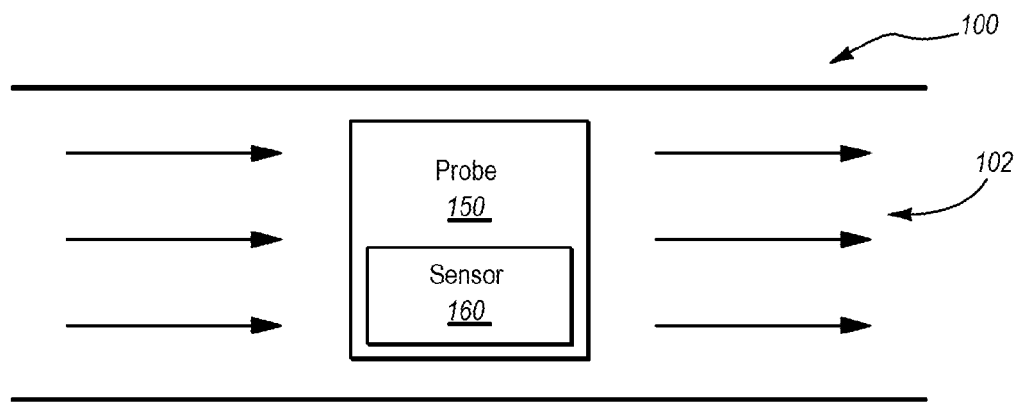
FIG. 1 illustrates an example of a probe deployed in a suitable environment.

Water quality is often defined in terms of the physical, chemical, and biological characteristics of water. Water quality is most frequently determined by reference to a set of standards against which compliance can be assessed. For example, turbidity is an attribute of a liquid that generally describes the opacity or cloudiness of the liquid (e.g., water). The turbidity of the liquid can be attributed to particles (e.g., solids) that are suspended in the liquid. There are many sources of turbidity including, but not limited to, human activities such as construction, mining, farming, waste dumping, and the like. Sediment, biological matter, algal growth, oxygen levels, light penetration, activities of aquatic life (e.g., stirring up the sediment), and the like can also contribute to the turbidity of a liquid.

Embodiments of the invention relate to extending the service interval of probes which determine the attributes and/or characteristics of a fluid (e.g. liquid or gas). More specifically, embodiments of the invention relate to probes that are equipped with antifouling control mechanisms. Example probes that are equipped with antifouling components or control include, but are not limited to, turbidity probes, temperature probes, pH probes, oxygen probes, conductivity probes, opacity sensor, stack gas sensor, optrodes, visibility meters, medical sensors, military sensors, and the like or any combination thereof.

Embodiments of the probes disclosed herein can provide multiple levels of antifouling control. Antifouling control can include the use of antifoulant components, material components, wiping control components, shutters, and/or light control components. While fouling of the probe may not be completely prevented, any fouling that the probe may experience can be limited or delayed such that the time between servicing of the probe is longer than it would be without the antifouling control mechanisms.

The probes disclosed herein thus include components that delay or prevent fouling in multiple ways. Example probes can delay or prevent fouling in multiple ways simultaneously or in a manner that overlaps in time. For example, the antifoulant components, the material components, the wiping control components, shutters, and/or the light control components can each act to delay or prevent fouling at the same time, and/or at different times while the probe is deployed in a suitable environment. As a result, the probes disclosed herein can measure attributes of a fluid, such as water, while extending the life and/or service period of the probes by preventing or at least delaying fouling of the probe.

A probe that is deployed in a fluid environment is often subject to fouling. The rate at which fouling occurs can impact the cost of maintaining the probe. A probe that experiences rapid fouling, for example, requires more frequent maintenance and may have to be replaced quickly. In comparison, a probe with antifouling control delays and/or prevents fouling of the probe. In this case, the probe does not need maintenance as frequently as a probe without antifouling control. This affects the time between servicing of the probe and may extend the life of the probe. Embodiments of the invention relate to probes with antifouling components that can prevent or at least delay fouling and thus extend the life of the probes or extend the time between servicing. Advantageously, cost savings can be achieved and the accuracy of the probe's measurements can be more reliable.

One of skill in the art can appreciate, with the benefit of the present disclosure, that embodiments of the invention can be adapted to different probes or other apparatus that may be subject to fouling. Embodiments of the invention are also discussed in terms of water (including salt water), although embodiments of the invention may be deployed in and/or configured for other fluids or other environments. Fouling material can be either organic or inorganic. Examples of fouling include, but are not limited to, biofouling including biological growth and aquatic growth, precipitation fouling including scaling and deposition, particulate fouling including silt buildup and dust and flue gas particulates, chemical reaction fouling including depositions of waxes and stains, and/or other fouling and the like or any combination thereof.

Embodiments of the invention also relate to keeping surfaces clean and to keeping at least some of the probe's surfaces clean or sufficiently clean so that the probe functions properly. Embodiments may include a feedback component that enables at least a portion of the probe to be cleaned. Although embodiments of the invention are described in the context of a probe that is deployed in a fluid, embodiments of the invention can also be used in other applications and environments.

There are many applications that use sensors or other measurement devices with surfaces that may require cleaning. In some instances, a probe and/or measurement devices may also have interfacial surfaces between a fluid and a surface of a probe (such as the sensor or surface of the probe that includes the sensor). The interfacial surfaces may also be subject to fouling and may require cleaning. Embodiments of the invention thus relate to systems and methods for cleaning at least one surface of a probe. In addition, embodiments can be adapted to clean portions of a surface as well. Examples of applications that may have surfaces requiring cleaning include optical applications, acoustical applications, chemical applications, and the like or any combination thereof.

For example, the optical power transmittance and reflectance of a probe should remain substantially constant to accurately measure light scattering (e.g., when measuring turbidity), light absorbance or spectral reflectance in a fluid sample. In a further example, the acoustic impedance of a surface should be substantially constant to measure target strength, acoustic backscatter and the range of remote objects. In yet another example the electro-chemical characteristics of a surface should be stable to accurately measure electrical potential and current flow between a reference electrode and a fluid sample. In another example, the chemical activity of an analyte in a fluid sample can be measured accurately by a solid-state chemical sensor, when the interface of the solid-state sensing elements is kept substantially clean.

There are many other situations where a surface should be maintained in a clean state and which are within the scope of the present invention. Examples of applications using probes with surfaces that may require cleaning include optical applications, acoustical applications, chemical applications, and the like or any combination thereof. More specifically, medical sensors (e.g., blood gases and chemistry), military sensors (e.g., forward looking infrared systems and detection of explosives and chemical agents in dirty environments), VIS and IR spectroscopy, visibility and fog meters (e.g., aviation, highway and maritime safety), stack gas and opacity sensors, solid-state fluid chemistry sensors, optrodes, laser metrology, scanning, and interferometry in environments, or the like or any combination thereof.

In these examples, a sensor or probe that includes a sensor may be used to sense, measure, or detect in the environment. Embodiments of the invention provide structure and methodology to sufficiently inhibit or prevent fouling, and/or clean surfaces of these sensors and/or probes such that their function is proper or to extend the time between servicing and/or replacement.

FIG. 1 illustrates an environment (e.g, a fluid such as water) suitable for deploying a probe that includes a sensor. The environment 100 typically includes a fluid. The environment 100 can include any type of fluid (e.g., gas, liquid), but is described herein with reference to water 102. In the context of water, the environment may be, by way of example only, an ocean, a lake, a river, reservoir, pipe, or other body of water regardless of size. One of skill in the art, with the benefit of the present disclosure, can identify other fluids or substances that may be included in the environment 100. The water 102 in the environment 100 may be flowing or stagnant.

In FIG. 1, a probe 150 has been deployed in the water 102. The probe may include a sensor 160. The sensor 160 may be configured to measure the turbidity of the water 102. The sensor 160 may alternatively be configured to measure other attributes of the water 102 including, but not limited to, the temperature of the water 102, salinity of the water 102, pH of the water 102, dissolved oxygen of the water 102, the depth of the probe 150, or the like or any combination thereof. Thus, the sensor 160 is typically configured to measure at least one attribute of the water 102. The measurement returned by the probe can be indicative of water quality or at least one aspect of water quality. For example, the measurement(s) returned by the probe 150 may be compared to a standard to ascertain the water quality.

In one example, the probe 150 is configured to measure the turbidity of the water 102 with a turbidity sensor 160. The turbidity measurements can be taken continuously, periodically, when requested, or the like or any combination thereof. The measurements taken by the sensor 160 in the probe 150 can be stored for later retrieval in memory, transmitted wirelessly or over a wired connection, or otherwise accessed. In addition, the probe 150 can be deployed in a manner that may be dependent on the sensor 160. For example, if turbidity is being measured, the probe 150 may be deployed and/or oriented in a position to minimize the impact of sunlight or in a manner that is suitable to taking the measurement. A probe 150 with the turbidity sensor 160, for instance, may hang downwards in the water 102 with the turbidity sensor 160 at the bottom.

Figure 2:
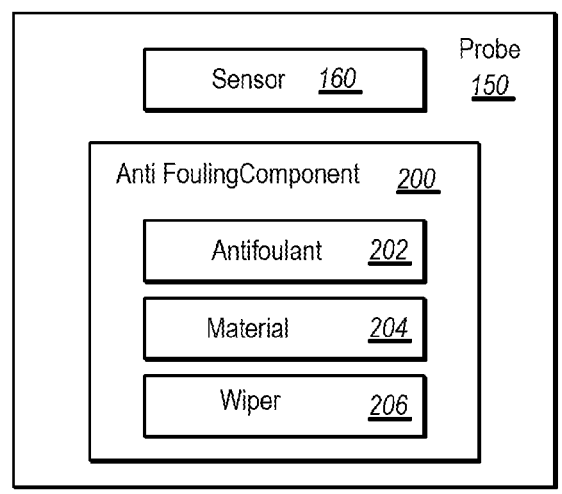
FIG. 2 illustrates a block diagram of a probe with antifouling control.

FIG. 2 illustrates a block diagram of the probe 150. As previously stated, the probe 150 includes a sensor 160 that may be configured to measure at least a turbidity (or other attribute or characteristic) of the water 102. The sensor 160 may measure turbidity by emitting light and then measuring the light that is scattered back to the sensor 160 (e.g., backscattering). Because turbidity can reflect an optical property of a fluid such as water, measuring the amount of light that is scattered and/or absorbed can thus measure the turbidity of the water 102.

In one example, the sensor 160 includes an optical emitter that emits light and optical detectors to detect light. The sensor 160 may thus include an emitter (e.g., a light emitting diode) and one or more detectors (e.g., photodiodes). The emitted light may be infrared or of another frequency and the detectors measure the light that is scattered. The measured light is then converted into a turbidity measurement. The conversion can be performed by the probe 150. Alternatively or in addition, the raw data can be stored by the probe 150 for later analysis. In some instances, the detectors may have a filter, such as a thin film filter, to ensure that ambient light does not interfere with the turbidity measurement.

FIG. 2 further illustrates that the probe 150 includes an antifouling component 200. The antifouling component 200 can prolong the expected service period of the probe 150 by preventing or at least inhibiting fouling of the probe 150. The structure and composition of the probe 150, including the antifouling component 200 are configured to extend the service period of the probe 150.

Generally, the antifouling component 200 operates to prevent, destroy, remove, kill, delay, or otherwise inhibit fouling. Fouling occurs, by way of example only and not limitation, when plant and/or animal life, mineral deposits, microorganisms, precipitates, silt, sediment, or the like or any combination thereof accumulate on a device such as the probe 150. Fouling thus includes biological fouling as well as non-biological fouling. As the fouling of the probe 150 increases, the ability of the probe 150 to function properly decreases. The fouling, for example, can begin to interfere with mechanical features of the probe 150 or prevent the sensors from taking accurate measurements. At some point, the probe 150 becomes essentially unusable because of the fouling.

For example, a turbidity probe operates by emitting light into the water and then detecting the light that is backscattered to the sensor. When plant life such as algae begins to accumulate on the surfaces of the probe, the plant life can adversely affect measurements taken by the probe. Light may be backscattered, for example, by the plant life instead of particles suspended in the water. As a result, the turbidity measurement is adversely affected. The antifouling aspects of the probes disclosed herein can delay or prevent fouling that adversely affects the probe or extend the service period of the probe before cleaning or replacement is required.

The antifouling component 200 illustrated in FIG. 2 may include an antifoulant component 202, a material component 204, and/or a wiper component 206. The antifouling component 200 may also include shutter components that aid in delaying or preventing fouling. The antifoulant component 202 may include an antifoulant (e.g., a biocide) that is toxic or poisonous to plant or other biological growth/life that may result in biofouling of the probe 150. The antifoulant component 202 may also include other antifoulants, such as scaling inhibitors that can inhibit, for example, nonbiological fouling. Thus, the antifoulants that may be included in the antifoulant component 202 may include, by way of example only, biocides, fungicides, algaecides, scaling inhibitors, or the like or any combination thereof. When the antifoulant is a biocide, the antifoulant component 202 may be referred to herein as a biocide component.

The antifoulant component 202 can be integrated into the body of the probe 105, or into paint or other covering of the probe 150. The antifoulant component 202 can include chambers formed in the probe that are configured to store and dispense the antifoulant. Some or all of the surfaces of the probe 150, for example, may be covered with a thin film that includes a biocide or other antifoulant. This type of thin film may deteriorate over time.

The antifoulant component 202 may also include an antifoulant that can be implemented as a solid or liquid that is released slowly over time. As described in more detail below, the antifoulant can also be stored in a chamber of the probe 150 to be released over time.

The wiper component 206 may include structure that is intended to perform a physical wiping and/or scraping action on at least the sensor 160 (and/or an area around the sensor 160) of the probe 150. For instance, the sensor 160 may include optical components (e.g. lenses, detectors, emitters) that can be at least partially cleaned or scraped by the wiper component 206. The wiper component 206 may include a wiper, brushes, mesh, a pad, or bristles, or the like or any combination thereof. The wiper component 206 can also be formed of a material that is selected based on the surface type of the probe 150 and/or on the anticipated fouling mechanism. For example, the materials used in the wiper component 206 for biological fouling may differ from the materials used for the wiper component 206 when precipitation fouling is anticipated.

In another example, the wiper component 206 may also include multiple materials. The materials can be arranged in rows. For instance, a coarse material may be followed by a less coarse material or by a more dense material or by another type of material that has different characteristics. One of skill in the art can appreciate that the materials included in the wiper component 206 can be selected based on the anticipated foulants. In addition, different materials may also work together to remove foulants. A first row of material may be configured to loosen a foulant such that a second row of material can remove the foulant. Each row can be moved over the portion of the probe being cleaned and each row can be more effective on different types of fouling. In one example, one row may be configured to remove biological foulants while another row may be configured to remove chemical foulants. One of skill in the art can appreciate, with the benefit of the present disclosure, that multiple variations of materials and arrangement of materials in the wiper component 206 are within the scope of the disclosure.

The wiper component 206 may also have an edge that is relatively sharp or hard. The wiper component 206 can remove biological growth, precipitates, stains, silt, and the like or any combination thereof, from the surface of the sensor 160 and/or from a surface of the probe 150. The wiper component 206 may be angled and provide superior scraping or wiping in a specific direction. In some examples, the wiper component 206 may be a replaceable pad that is adhered to the surface of the probe in a manner to wipe the sensor 160 as described herein.

The material component 204 is another antifouling component that can cooperate with the wiper component 206 to prevent or delay fouling. The material component 204 can prevent or at least inhibit biological (e.g., biological growth such as algal growth) and/or non-biological fouling (e.g., staining, organic/inorganic dyes, chemical precipitates, particles, scaling, or the like). In one example, material component 204 is placed in specific locations of the probe 150. The material component 204 is typically formed from a material that inhibits or prevents fouling. The material component 204 may include, for example, metals such as copper, copper alloys, coin silver, silver plates, and the like that are positioned to prevent or inhibit fouling of the probe 150 or portions thereof. The material component 204 may be used to form the body of the probe 150 or at least a portion of the probe 150 and/or the body of the sensor or at least a portion of the sensor 160 The material component 204 can be placed in various locations that can aid in extending the service period of the probe 150.

FIGS. 3A and 3B illustrate an example of the probe 150 that includes a portion 302 and a portion 304. The portions 302 and 304 cooperate to prevent or delay fouling of the sensor 160 and/or of the probe 150. FIGS. 3A and 3B also illustrate an example of the wiper component 206. As the portion 304 translates relative to the portion 302, the wiper component 206 operates to clean the sensor 160.

The portion 304 (or the portion 302) may move or be displaced for several reasons. The portion 304 may be displaced, by way of example, to expose the sensor 160 to the environment 100 and/or to perform maintenance/cleaning on the sensor 160. The sensor 160 is exposed when the probe 150 is in an open position as illustrated in FIG. 3B. In the open position, attributes of the water (or other suitable liquid/environment), such as turbidity, temperature, conductivity, oxygen, etc., may be measured by the sensor 160. When the probe 150 is in a closed position, as illustrated in FIG. 3A, the sensor 160 may be covered by the wiper component 206 or be located adjacent to the wiper component 206. As the portion 304 transitions from the open position to the closed position, the wiper component 206 can clean the sensor 160. More specifically, the lateral translation of the portion 304 causes the wiper component 206, which is typically pressed against the sensor 106, to wipe or scrape the sensor 160 clean. A similar cleaning action occurs when the portion 304 transitions from the closed position to the open position.

In this example, the probe 150 can shutter the sensor 160 behind the wiper component 206 or other aspect of the portion 304 and shield the sensor 160 as well as the front surface of the portion 302 from light. In other words, the portions 302 and 304 may also be configured to minimize the light from striking the area of the probe around the sensor 160. Shuttering the sensor 160 in this manner can prevent light or reduce the light that reaches the sensor 160 or the area surrounding the sensor 160. Thus, shuttering the sensor 160 can inhibit fouling including biofouling, for example by inhibiting growth that may rely on light. Shuttering also inhibits biological or sediment components access to the sensor, thus inhibiting fouling.

FIGS. 3A and 3B also illustrate a mechanical aspect of the probe 150 that operates at least in conjunction with the wiper component 206. As previously stated, FIG. 3A illustrates the portions 302 and 304 in a closed position while FIG. 3B illustrates the portions 302 and 304 in an open position. The portion 304, however, is able to move relative to the portion 302, although the probe 150 can be configured such that the portion 302 moves relative to the portion 304. The portions 302 and 304 may be configured to engage in a manner that prevents the portions 302 and 304 from being separated but allows the portions 302 and 304 to translate laterally with respect to each other such that the probe 150 can move from the open position to the closed position and vice versa.

The sides of the portions 302 and 304 may have a tongue and groove arrangement that enables translation of the portion 304 relative to the portion 302 while maintaining the wiper component 206 in a position to clean the sensor 160. In one example, the wiper component 206 may include a material that is compressible and that extends out from the surface of the portion 304. By extending out from the surface, the wiper component 206 can physically contact the sensor 160 and the corresponding surface of the portion 302 as the portions 302 and 304 translate between the open position and the closed position.

More specifically, to maintain the structural relationship between the wiper component 206 and the sensor 160, the portion 302 may have a groove or notch that is engaged by an edge or projecting rib formed in the portion 304 or vice versa. The connection between the portions 302 and 304 enables translation between and from the open and closed positions while preventing the portions 302 and 304 from being separated (as illustrated in FIG. 4). The portions 302 and 304 may thus be slidably connected to permit this type of movement. The groove may also include stops to control how far the portions can move laterally and to prevent inadvertent separation. One of skill in the art can appreciate other engaging or complimentary structure that permit the motion of the portions 302 and 304 described herein.

FIG. 4 illustrates an expanded view of the probe 150 with the portion 302 separated from the portion 304 for illustration purposes. The portion 302 includes sensor components 310, which form at least part of the sensor 160. The sensor components 310, in this example, include optical components that are positioned substantially flush with the surface 312 or slightly recessed and/or angled, although a clear window that is flush with the surface 312 may be present to protect the sensor 160. As a result of the sensor 312 being substantially flush with the surface 312, the surface 312 and the surface 316 can slide relative to each other without adversely affecting the sensor 310.

In addition, each or one of the portions 302 and 304 may be sealed such that water cannot enter the interior 314 of the portion 302 or the interior 318 of the portion 304. Alternatively, each or one of the portions 302 and 304 may be open or partially open to the environment and may allow a liquid such as water to enter therein into the interior 314 and/or 318.

In this example, the sensor 160 is substantially disposed in the interior 314 of the portion 302 and the sensor components 310 are exposed in the surface 312 often via a clear window. Thus, the sensor components 310 can be exposed to the environment to take measurements when the portions 302 and 304 are in the open position. The portion 302 is typically sealed such that any electronics or other components of the sensor 160 are protected from the environment or from water. In this example, the sensor components 310 are embedded in the surface 312 in a manner that prevents water or other liquids from entering the interior 314. For example, the components 310 may be optical emitters or detectors 320, lenses and the like. In addition, films that cover the optical emitters or detectors 320 may also be present. The interface between the components 320 and the surface 312 is sealed, by a clear window, in one example to be substantially waterproof.

The interiors 314 and 318 may also be compartmentalized in some examples. This may allow a substance such as a biocide to be stored inside of the portions 302 and/or 304 and released over time through appropriate passages or apertures in the portions 302 and 304. In one example, the surfaces 312 and 316 may be painted with a paint that includes a biocide. This enables the biocide to be released over time.

Figure 5A:
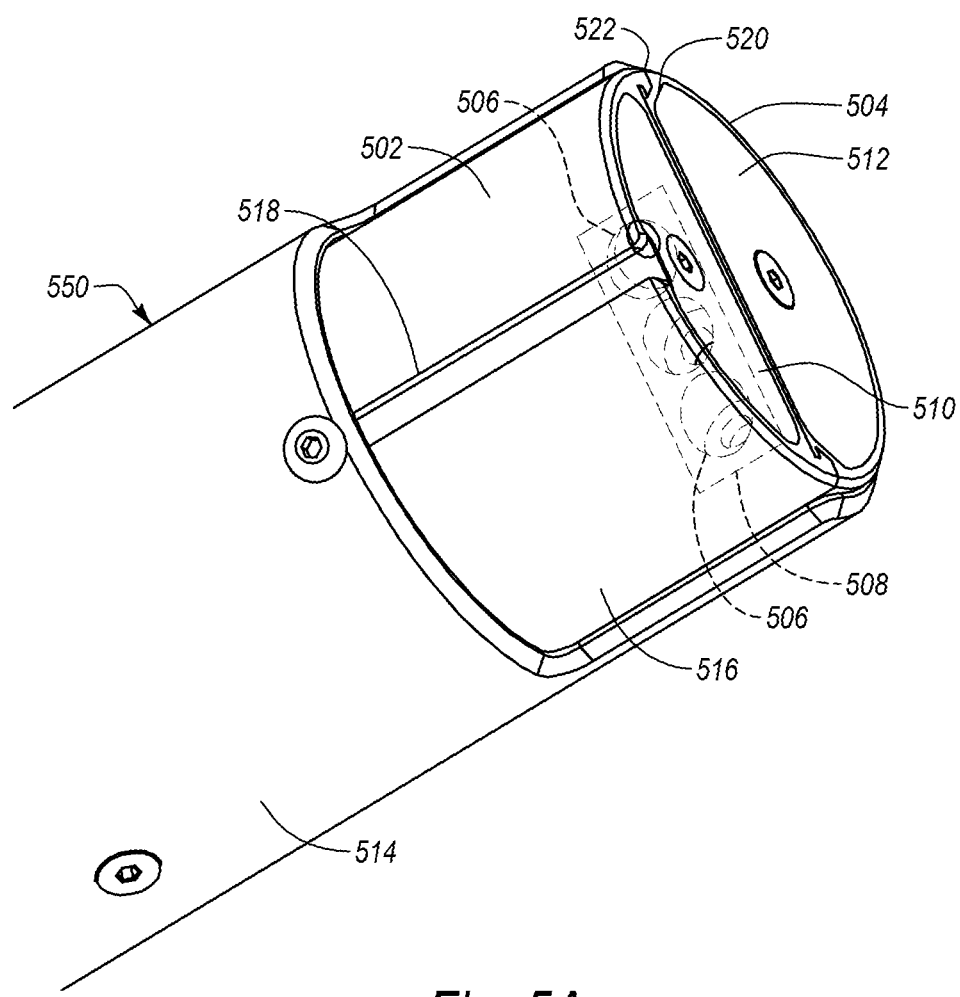
FIG. 5A illustrates an example of a probe in a closed position with antifouling components.
Figure 5B:
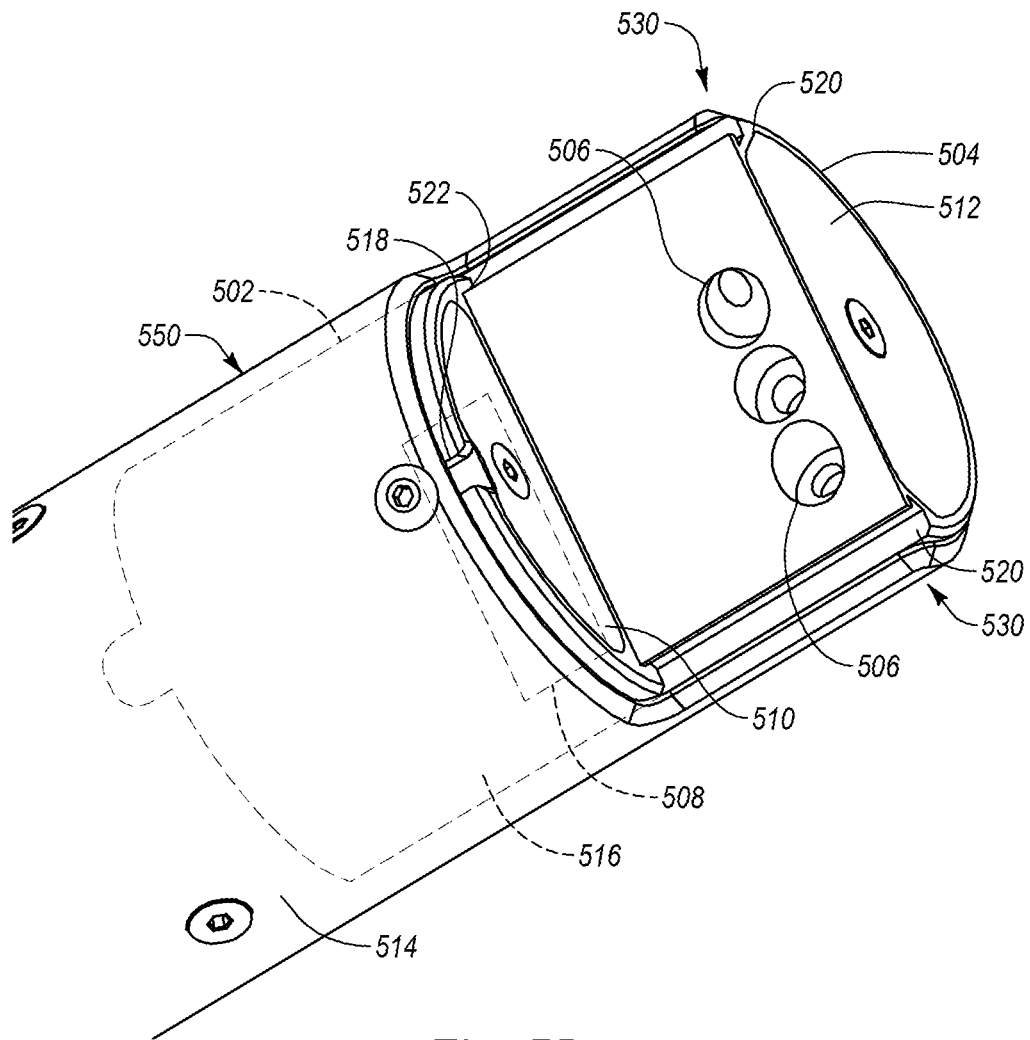
FIG. 5B illustrates an example of the probe in FIG. 5A in an open position.

With reference to FIGS. 5A and 5B, FIG. 5A illustrates a perspective of the probe 550, which is an example of the probe 150, in a closed position and FIG. 5B illustrates the probe 550 in an open position. The probe 550 includes a portion 502 and a portion 504. The portion 502 can move from a closed position to an open position. When in the open position, the sensor 506 is exposed and a measurement can be taken using the sensor. As the probe transitions from the open position to the closed position, the wiper component 508 can act to clean at least the sensor 506. More specifically, the wiper component 508 is secured to the portion 502 or is an integral part of the portion 502. As a result, movement of the portion 502 results in movement of the wiper component 508. The wiper component 508 is thus positioned on the portion 502 such that the sensor 506 is cleaned when the portions 502 and 504 of the probe 550 transition to the open position and/or when the portions 502 and 504 transition to the closed position. In addition, the wiper component 508 is positioned on the surface of the portion 502 to shutter the sensor 506 when the probe 550 is in the closed position. The sensor 506 is typically located near the end 530 of the probe 550. This helps ensure that the portion 502 does not interfere with the operation of the sensor 506 when in the open position. The dimensions of the portions 502 and 504, the amount of retraction of the portion 502, and other dimensions of the probe 550 can be selected to ensure proper operation of the sensor 506.

The tops of the portions 502 and 504 may include or be formed from materials 510 and 512. The materials 510 and 512 may be repellant or distasteful to biological life (e.g., plants, algae, mollusks, larvae) and thus provide a level of fouling control including biofouling control. In the closed position, the body of the portions 502 and 504 may be at least partially disposed in a body 514 of the probe 550. As a result, the materials 510 and 512 (e.g., copper, silver, etc.) provide biofouling control. Other portions of the portions 502 and 504 or other parts of the probe 550 may also be formed from the materials used in the tops of the portions 502 and 504.

The material 510, as previously stated, can inhibit biological growth on the surface of the material 510. If this growth were permitted, the growth could interfere with measurements taken by the sensor 506. Similarly growth on the surface of the material 512 could also interfere with the operation of the sensor 506. For instance, water current could cause the growth to move in front of the sensor 506 or to reflect light back to the sensor 506. In this sense, the materials 510 and 512 provide antifouling to the probe 550 by preventing biological growth at an area that is not immediately adjacent the sensor 506.

FIGS. 5A and 5B also illustrate that the portion 502 includes a wiper 508, which is an example of a wiper component 206. The wiper 508 is usually at least as wide as the portion of the sensor 506 that is exposed on the surface of the portion 504. The wiper 508 may include a rubber (or other suitable material) blade that can clean at least the exposed portion of the sensor 506 in one example. Alternatively, the wiper 508 may also include bristles in some embodiments or a mesh material. In some examples, the probe 550 may include a cleaning mode that repeatedly moves the portion 502 so as to repeatedly scrape or clean the sensor 506. This provides additional cleaning that may not be achieved when the wiper 508 is used only when measurements are taken by the sensor 506.

FIGS. 5A and 5B further illustrate that the body 514 of the probe 550 can be shaped to accommodate the portions 502 and 504. In this example, the portion 504 is disposed inside of the body 514 or is placed adjacent to the body 514. The body 514 has a cut out portion such that when the portion 502 is retracted, the sensor 506 can take a measurement without interference from the body 514. More specifically, the portion 502 is exposed to the environment in the closed position and is adjacent to the body 514 when in the open position. In one example, the portion 502 is substantially enclosed within the body 514 when in the open position.

As a result, the exterior surface of the portion 504 is protected from the environment by the body 514. The top of the portion 504 is covered with the material 512. Although the surface of the body 514 may experience more fouling than the material 512 (when the material of the body 514 is different, for example for cost reasons), the operation of the probe 550 is unaffected by such fouling because the fouling on the body 514 is much less likely to interfere with the operation of the sensor 506. However, the body 514 may have a layer of the material component that inhibits fouling or be painted with a paint that includes biocide, for example.

In this example, the exterior surface of the portion 502 may be exposed to the environment when in the closed position. More specifically, the body 514 on the side of the portion 502 does not extend as far as the body 514 on the side of the portion 504 when the probe 550 is in the closed position. The body 514 is shaped in this manner so that the sensor 506 can be exposed when the portion 502 is retracted as previously described. As a result, the surface 516 of the portion 502 can be formed from a material similar or the same as the material 510 that provides antifouling. Additionally, the body 514 may scrape the surface 516 as the portion 502 is retracted and extended.

Alternatively, the probe 550 may be configured such that the portion 504 is extended when a measurement is taken. In this case, the body 514 may not have a cut-out portion. In addition, the body 514 would similarly protect the surface 516 when the probe 550 is in a closed position. In the closed position, the materials 510 and 512 would be exposed to the environment but are less likely to experience fouling because they are formed of a material that resists fouling.

FIGS. 5A and 5B illustrate that the movement of the portion 502 may be guided by a groove 518. The groove 518 may provide a track to aid in the sliding movement of the portion 502. The groove 518 may cooperate with a rib that is formed in the body 514. FIGS. 5A and 5B further illustrates that the portion 502 engages the portion 504 with a groove 520 and tongue 522 arrangement. The groove 520 and tongue 522 enable at least one of the portions 502 and 504 to move laterally with respect to the other without separating as previously described.

FIGS. 5A and 5B thus illustrate that the probe 550 includes multiple antifouling components. The wiper 508 provides a wiper component that can clean the sensor 506 when the probe 550 moves between the open and closed positions. This can include cleaning biological growth, precipitates, stains, and the like. In addition, movement of the portion 502 can cause movement of the water or fluid to wash or flush away debris or growth that has been removed. The materials 510 and 512 can inhibit at least biological growth that may interfere with the operation of the probe 550. The movement of the portions 502 and 504 also provide a shuttering action that can prevent light from reaching the sensor 506 and surrounding area when in the closed position and keep aquatic growth off the sensor 506.

Also, as described in more detail below, a biocide can be delivered to at least the sensor 506 to keep it free of biological growth, and/or an area beneath the portion 502 (the space occupied by the portion 502 when the probe is in the open position). Delivering biocide to the area beneath the probe 502 can prevent or delay fouling that may interfere with the opening and/or closing of the probe 550. The portion 502, the portion 504, and the antifouling components are an example of a sensor module that can be disposed in a body of a probe.

Figure 6:
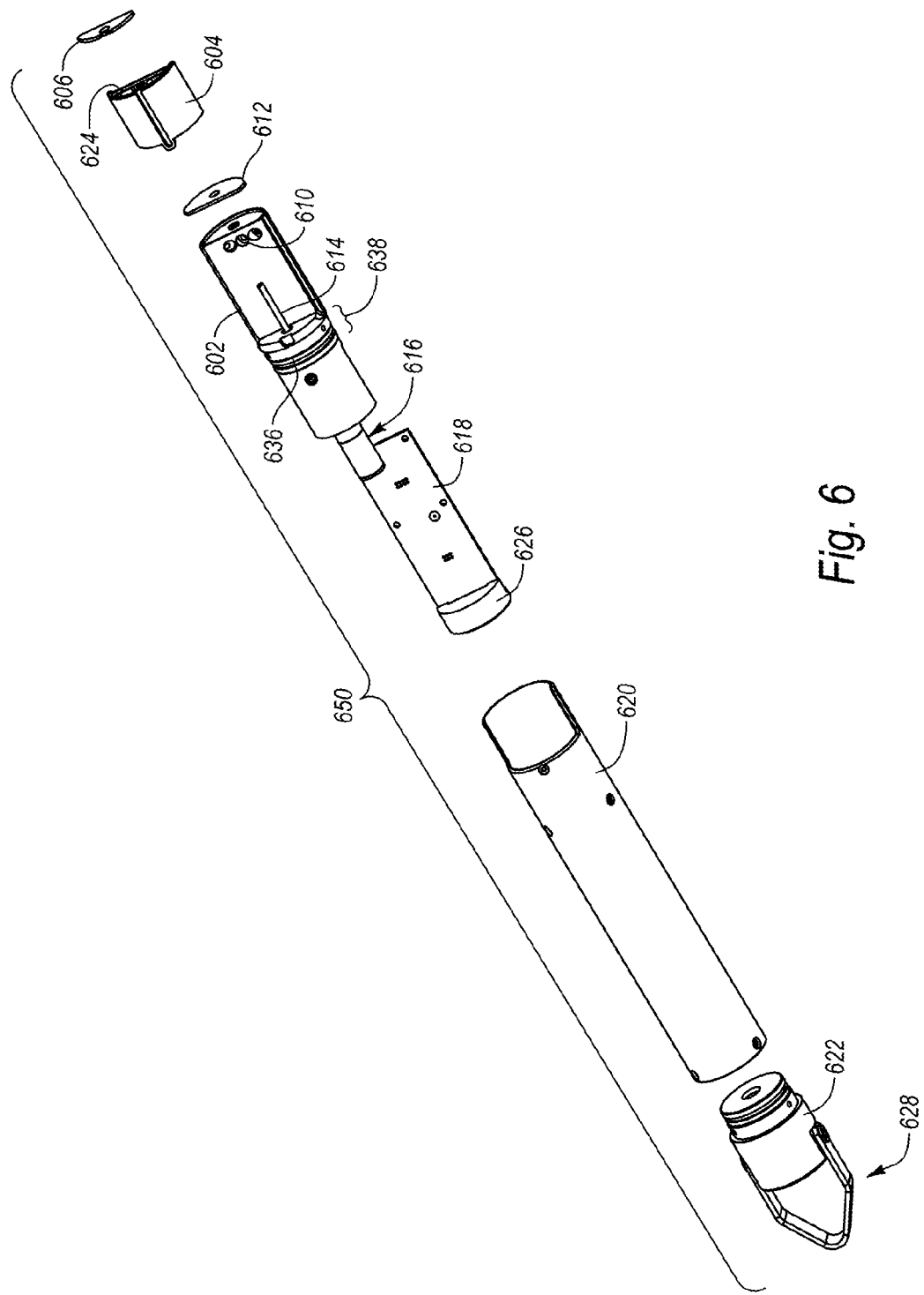
FIG. 6 illustrates an expanded perspective view of a probe with antifouling components.

FIG. 6 illustrates an expanded perspective view of a probe 650, which is an example of the probe 550 or the probe 150. In this example, the probe 650 can be assembled with suitable connectors as needed (e.g., screws) Other connectors may also be used. The probe 650 includes a body 620 that is sized to accommodate the sensor 610 and accompanying electronics. A cap 622 can seal one end of the body 620. The cap 622, which may be coated with an antifouling material, may be attached to a cable that may provide an electrical connection between the sensor 610 in the probe 650 and a remote location. A wire connection in the cable (or a fiber optic connection) can be used to retrieve data from the probe, configure the probe via software updates, and the like. A rope/cable attached to handle 628 can be used to deploy the probe 650 or retrieve the probe 650.

The sensor 610 is typically connected to a circuit board 618, which includes components to operate the sensor 610. The circuit board 618 may also include components to control a motor 616. The motor 616 drives a shaft 614, which may be threaded in one example, to move the portion 604 relative to the portion 602. The motor 616 can rotate the shaft 614 and thus retract or extend the portion 604 such that a measurement can be taken with the sensor 610. A seal 636 interfaces with the body 620 to prevent water from adversely affecting the circuit board 618. FIG. 6 further illustrates materials 606 and 612 that provide antifouling control similar to the materials 510 and 512.

Figure 7:
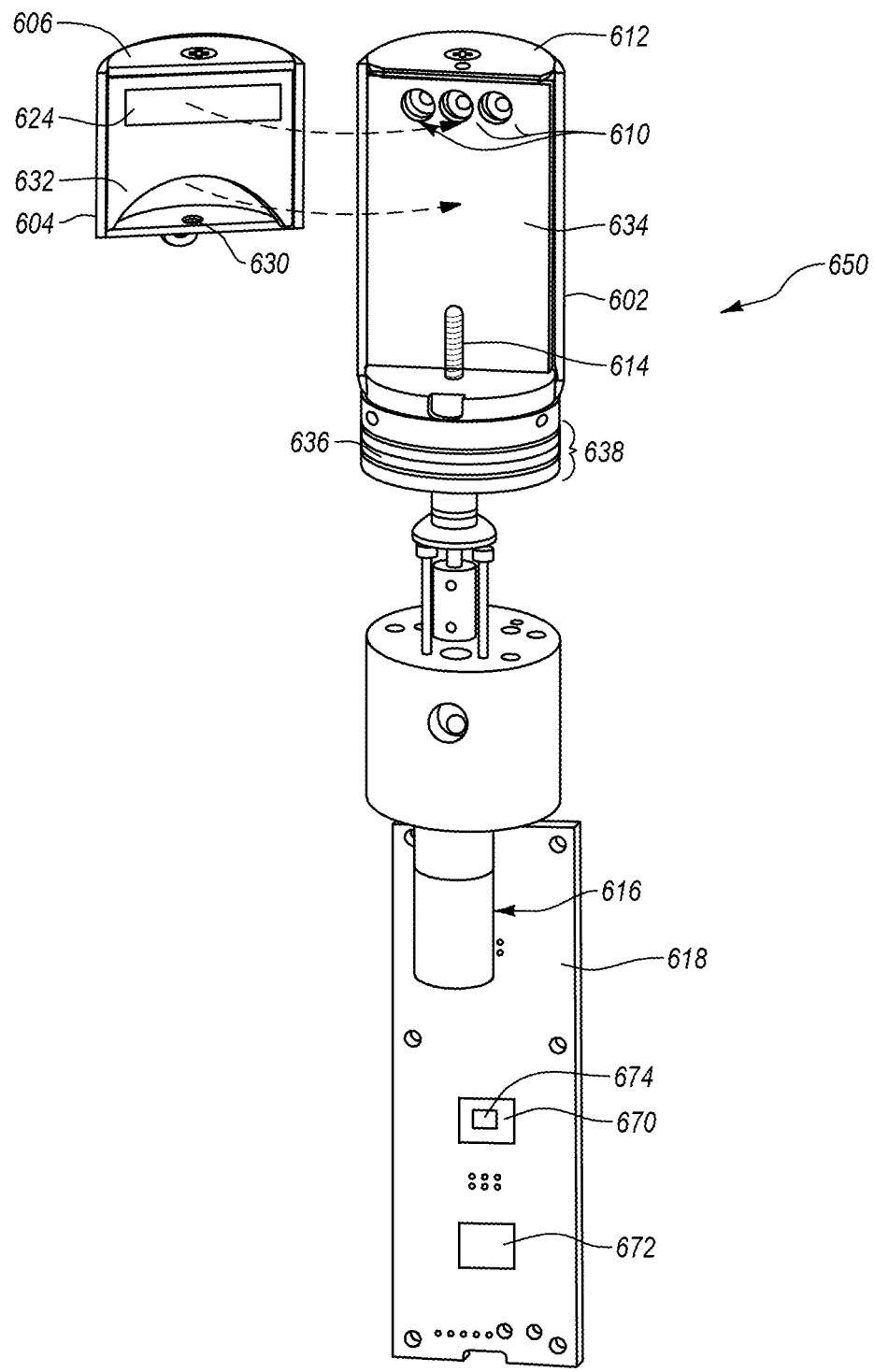
FIG. 7 illustrates a perspective of a probe including a wiping component.

FIG. 7 illustrates the probe of FIG. 6 with an alternate view of the portion 604. The portion 604 is illustrated to depict the wiper 624, which is an example of the wiper component 206. The wiper 624 can be positioned at any location of the surface 632. Similarly, the sensor 610 can also be exposed at any location on the surface 634. In one example, the sensor 610 and the wiper 624 are positioned such that the sensor 610 is scraped or cleaned when the portion 604 is translated laterally relative to the portion 602. As previously described, the wiper 624 may wipe or clean the sensor 610 in both directions.

In one example, the circuit board 618 or a controller 674, which controls the motor 616, can measure the amount of current it takes to position the wiper 624. The amount of current required to drive the motor 616 may be used to determine if the surface of the sensor 610 requires additional cleaning or to determine that the sensor is potentially fouled or at least partially fouled. For example, when additional current is sensed, the controller on the circuit board 618 can determine that the portion 604 should be moved back and forth one or more times in an attempt to clean or remove whatever is causing the increased current. For example, the fouling may be on the shaft 614 that is exposed to the water or on the surface 632 or on the surface 634, or in another location of the probe 650. This fouling may cause difficultly in opening or closing the probe (e.g., moving between the open position and the closed position), which results in increased current to drive the motor. The additional current can be sensed by comparing the current required to drive the motor exceeds a predetermined or threshold current.

In addition, the portions 602 and 604 are typically sized and configured such that the sensor can be sufficiently exposed to take accurate measurements of the water's attributes, which may include turbidity. FIG. 7 illustrates that the portion 604 is smaller (e.g., has less length) than the portion 602. This allows the shaft 614 to cooperate with the shaft engagement 630 (e.g., in a threaded arrangement) to retract and extend the portion 604. When the portion 604 is lowered or retracted (as illustrated in FIG. 5B), the sensor 610 is exposed for performing measurements. When the portion 604 is raised by the motor 616 and the interaction of the shaft 614 and the shaft engagement 630, the sensor 610 is covered by the wiper 624.

When the portion 604 is retracted or raised, the associated movement can cause water to move past the sensor 610 and help clean the sensor 610 or other part of the probe 650. This movement flushes away debris, sediment, removed foulants, and the like. In one example, the movement of the portion 604 can flush the sensor 610. In some instance, the portion 604 may be configured to flush the sensor 610 by directing the fluid to a specific location on the probe 650. One or more fins or other flushing structures on the portion 604, for example, can be used to control the flushing of the probe 650 during movement of the portion 604.

When the probe 650 is in a closed position, the ability of light to reach the sensor 610 or the area immediately surrounding the sensor including the surfaces 632 and 634 is reduced. The portions 602 and 604 may be configured with seals intended to prevent light, water, aquatic life, etc., from reaching the sensor 610 when in the closed position. Advantageously, shuttering the probe 650 in this manner slows or prevents fouling including biofouling.

The probe 650 also includes a sealed enclosure 620 that protects the electronics of the board 618 and/or the motor 616 from water when the probe 650 is assembled. The body or enclosure 620 (see FIG. 6), which may be sealed, may be coated with an antifouling material. A seal such as an O-ring 636 that cooperates with the enclosure 620 may also protect the internal electronics from water.

The portion 602 may also be sealed and have an internal passage that permits electronic components to connect the sensor 610 with the circuit board 618. More specifically, the bottom 638 of the portion 602 may include openings to permit the circuit board 618 or components mounted thereon to electrically and/or mechanically connect with the sensor 610. Because the portion 602 is sealed, water cannot enter into the interior of the portion 602.

The probe 650 may also include a controller 674 that is used to control the operation of the probe 650. As described in more detail below, the controller 674 may also be included in a feedback component 670. The feedback component 670 can be implemented in hardware and/or software. The controller 674 may be mounted on the circuit board 618, along with other components including, but not limited to memory 672, drivers, and the like. The controller 674 can, for example, cause the probe to move to an open position, take a measurement, store the measurement, and move the probe to a closed position. The controller 674 may have access to memory and be able to log measurements over time. This allows the results to be retrieved at different times and not necessarily at the time the measurement was taken. The controller 674 may also log other information about the operation of the probe 650 and/or the sensor 610. The controller 674 can measure parameters of the probe 650 including, but not limited to, current, voltage, position, or the like or any combination thereof. In another example, the parameters of current and/or voltage may relate to the movement of the probe when moving from the open position to the closed position. The controller 674 may log current and/or voltage measurements that can be used to determine when the probe 650 should receive maintenance or be replaced or serviced.

When a measured parameter exceeds a threshold value (e.g., a measured current or voltage exceeds, respectively, a current threshold or a voltage threshold), then the controller 674 may perform a predetermined action—such as cleaning the at least a portion of the probe. In addition, these measurements can also be converted into other values such as power, torque, and the like, which may also be used by the controller 674 and/or the feedback component 670 to operate and/or maintain the probe 650.

The probe 650 may also include the feedback component 670 that can be used in the operation of the probe 650. The feedback component 670 typically includes the controller, which is used to measure aspects of the probe 650 during operation of the probe. These measurements can be used by the probe 650 to enhance the operation, for example by extending the service period of the probe.

As previously mentioned, the controller 674 can measure the amount of power it takes to translate move the portion 604. The amount of power required to drive the motor 616 may be used to determine if the surface of the sensor 610 requires additional cleaning and then initiate this cleaning by moving the wiper over the sensor multiple times. Thus, the feedback component 670 can use the controller 674 to determine that the sensor or other surface of the probe that includes the sensor, or other portion of the probe may require additional cleaning.

In this example, the feedback component 670 measures the power (or current) to translate the portion 604 and determines that the surface of the sensor 610 or the surface of an area around the sensor may be fouled. The feedback component 670 then directs that the wiper be moved back and forth over the sensor or other area. Thus, the portion of the probe that is cleaned by the feedback component 670 may or may not include the sensor.

Alternatively or in addition, the feedback component 670 could direct that additional biocide be delivered to the sensor. The feedback component 670 could also control the speed and/or pressure with which the probe 650 transforms from the closed position to the open position or vice versa. Moving the portions of the probe with more speed, for example, may dislodge a precipitate that may not be dislodged at lower speeds.

Alternatively or in addition, the feedback component 670 could cause the wiping component to be pressed with greater pressure. Applying greater pressure, while scraping or wiping the sensor in one example, may result in more effective cleaning. In one example, the probe 650 may be configured to press the wiper 624 against the surface 634 with more pressure. The wiper 624 may have a soft or pliable outer layer and a harder less pliable inner core. As a result, applying the wiper 624 with greater pressure against the surface 634 can engage the less pliable or harder inner core of the wiper 624 in the cleaning process performed by the probe 650.

As previously mentioned, the feedback component 670 could detect fouling at any position between the open position and the closed position. The feedback component 670 can therefore direct that any part of the surface 634 be cleaned, for example by moving the wiper 624 across that particular part repeatedly. The specific part of the surface 634 can include the area of the surface 634 where the sensor 610 is exposed. Of course, the area being cleaned in this manner (e.g., by wiping repeatedly and/or applying more pressure while wiping) may not include the sensor 610.

When determining a corrective action (such as moving the wiper back and forth over the sensor), the feedback component 670 can measure the power or the current required to move the sensor from the open position to the closed position. The feedback component 670 can also consider sensor measurements that are unexpected or that fall outside of a predetermined range. The feedback component 670 may also use the wiper component more frequently when the antifoulant component is exhausted or empty and not yet refilled. In one aspect, the feedback component 670 dynamically adapts to changing conditions of the probe to ensure and/or extend operation of the probe.

The circuit board 618 may also include a transmitter such that information can be transmitted wirelessly when possible.

Figure 8A:
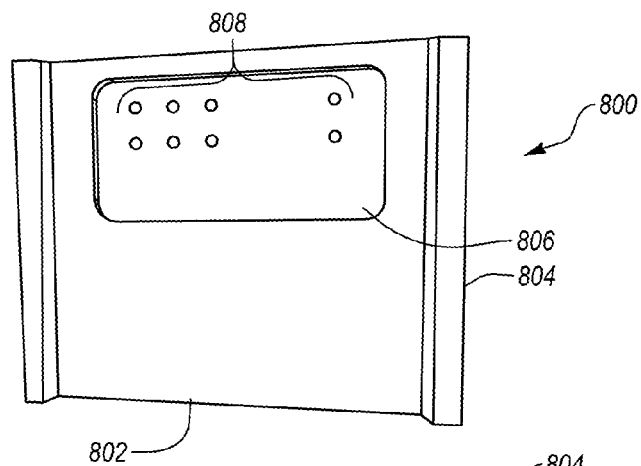
FIG. 8A illustrates a front view of a portion of the probe including a portion of a wiping component.
Figure 8B:
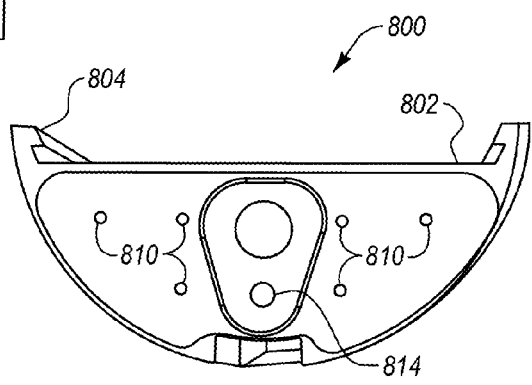
FIG. 8B illustrates a bottom view of the portion of the probe in FIG. 8A.
Figure 8C:
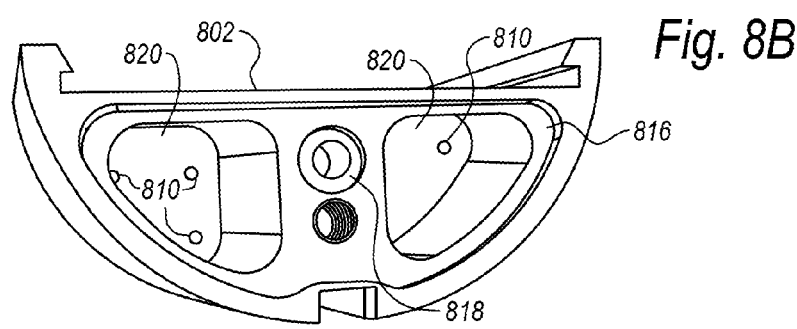
FIG. 8C illustrates a perspective view of the portion of the probe in FIG. 8A and illustrates chambers for storing antifoulants.
Figure 8D:
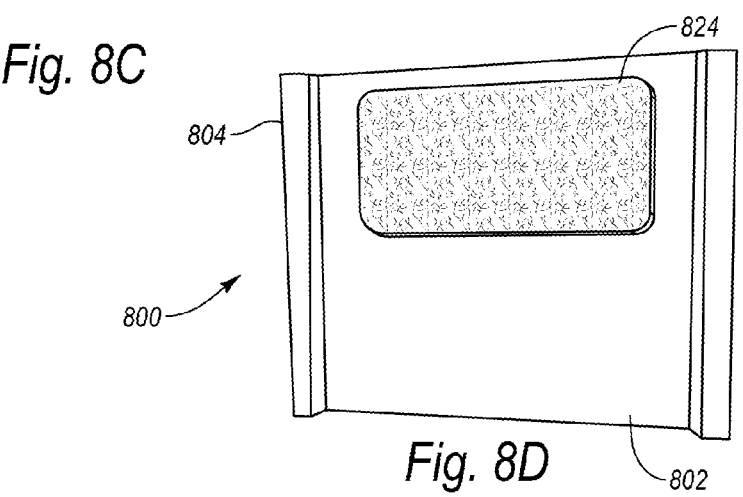
FIG. 8D illustrates a perspective view of the probe in FIG. 8A showing a wiping component in front of the holes.

FIGS. 8A, 8B, 8C, and 8D show an illustrative example of a portion 800, which is an example of the portion 604, 502, or 304. FIG. 8A illustrates a view of the surface 802, which is located adjacent, for instance, a surface of the portion 602 that includes the sensor 610 when the probe is assembled. The space 806 is formed in the surface to accommodate a wiper, such as the wiper 824 in FIG. 8D. FIG. 8D illustrates that the space 806 is formed to receive the wiper 824 and that the wiper 824 is sized and configured to fit in the space 806. One of skill in the art can appreciate, however, that the space 806 may not be present and that the wiper 824 can be adhered to the surface 802.

Thus, the space 806 may be slightly indented in the surface 802 or not. The space 806 is typically sized to receive and secure the wiper 824. The wiper 824 can be affixed by a waterproof and/or saltwater proof adhesive. When assembled, the wiper 824 may extend above the surface 802 to insure contact with the sensor during operation of the sensor as described herein. In one embodiment, the tongue and groove arrangement ensure that the wiper 824 is sufficiently pressed against the sensor or against the surface in which the sensor is exposed. By pressing the wiper 824 against this surface or ensuring that the wiper 824 contacts the surface, the sensor can be cleaned by the wiper 824 as the probe transitions from the open position to the closed position.

FIG. 8B illustrates the tongue 804 that cooperates with a groove of another portion as previously described. In fact, with reference to FIG. 6, the portion 602 and the portion 604 may each have a tongue and groove configuration that are configured to slidably engage each other. The engagement 814 engages with a shaft of a motor that can raise and lower the portion 800.

FIG. 8C illustrates that the portion 800 includes one or more chambers 820. In this example, an antifoulant can be placed in the chambers 820. The antifoulant could be a biocide (e.g., bromide, chloride, pepper or capsaicin), a scaling inhibitor, or other type of antifoulant. The antifoulant may be in a crystal or pellet form or other solid form or liquid form. A material, such as the material 606 is then placed on the portion 800 to secure the antifoulant in the chambers 820. Although the chambers 820 are illustrated as being within the portion 800, one of skill in the art can appreciate configurations where the chambers are external to the body of the probe.

The following discussion refers to biocide being stored in the chambers 820. One of skill in the art can appreciate, with the benefit of the present disclosure, that the chambers 820 may contain other antifoulants. In one example, the chambers 820 may be used to dispense at least two antifoulants at the same time.

In this example, the portion 800 is configured such that water is able to enter the chambers 820. As a result, the stored in the chambers 820 can dissolve over time. The biocide is then permitted to exit the chambers 820 via the apertures 808 and 810. When the probe is in the closed position, the biocide exits the apertures 808 which are positioned to effectively bathe the sensor in a biocide solution to prevent fouling. Similarly, the area below the portion 800 also receives biocide. This may keep, for example, the sides of the body of the probe and the shaft from fouling so that movement of the portion 800 can be accomplished more easily. The biocide can be formulated (e.g., by controlling the size of the crystals, the concentration of the biocide in the crystals and/or the solubility of the crystals) to control the rate at which the biocide is delivered. The chambers 820 can then be refilled over time to continue providing antifouling control. In one example, the wiper 824 becomes saturated with biocide and is able to wipe the surface 634 as well as the sensor 610 to perform antifouling control.

Figure 9B:
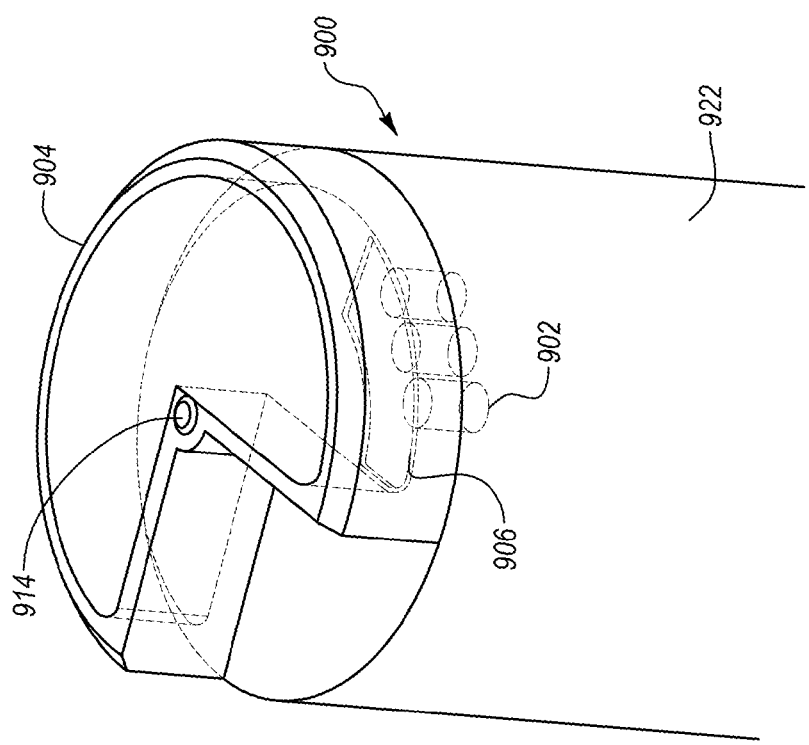
FIG. 9B illustrates the probe in FIG. 9A in an closed position.
Figure 9A:
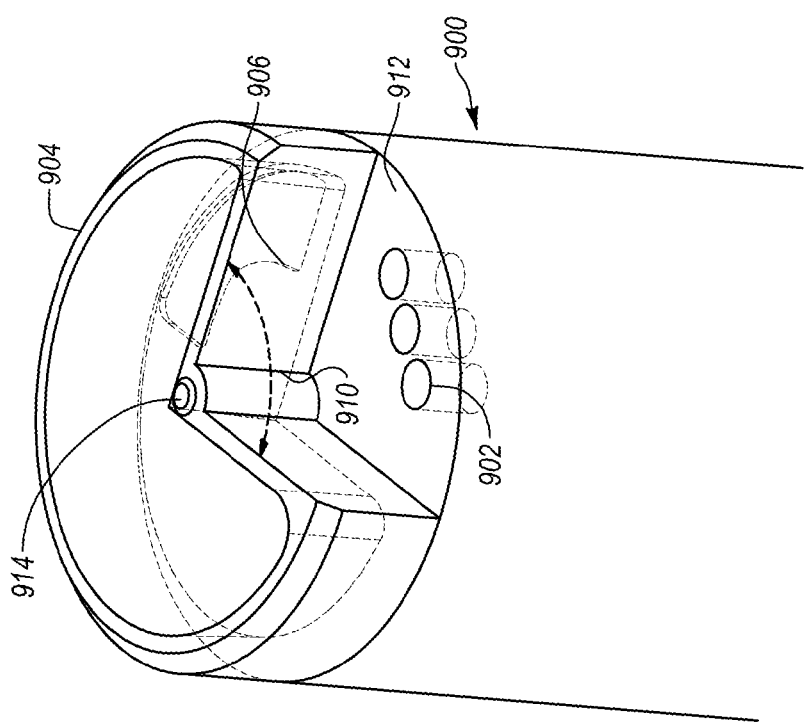
FIG. 9A depicts an another embodiment of a probe in a open position with antifouling components.
Figure 9C:
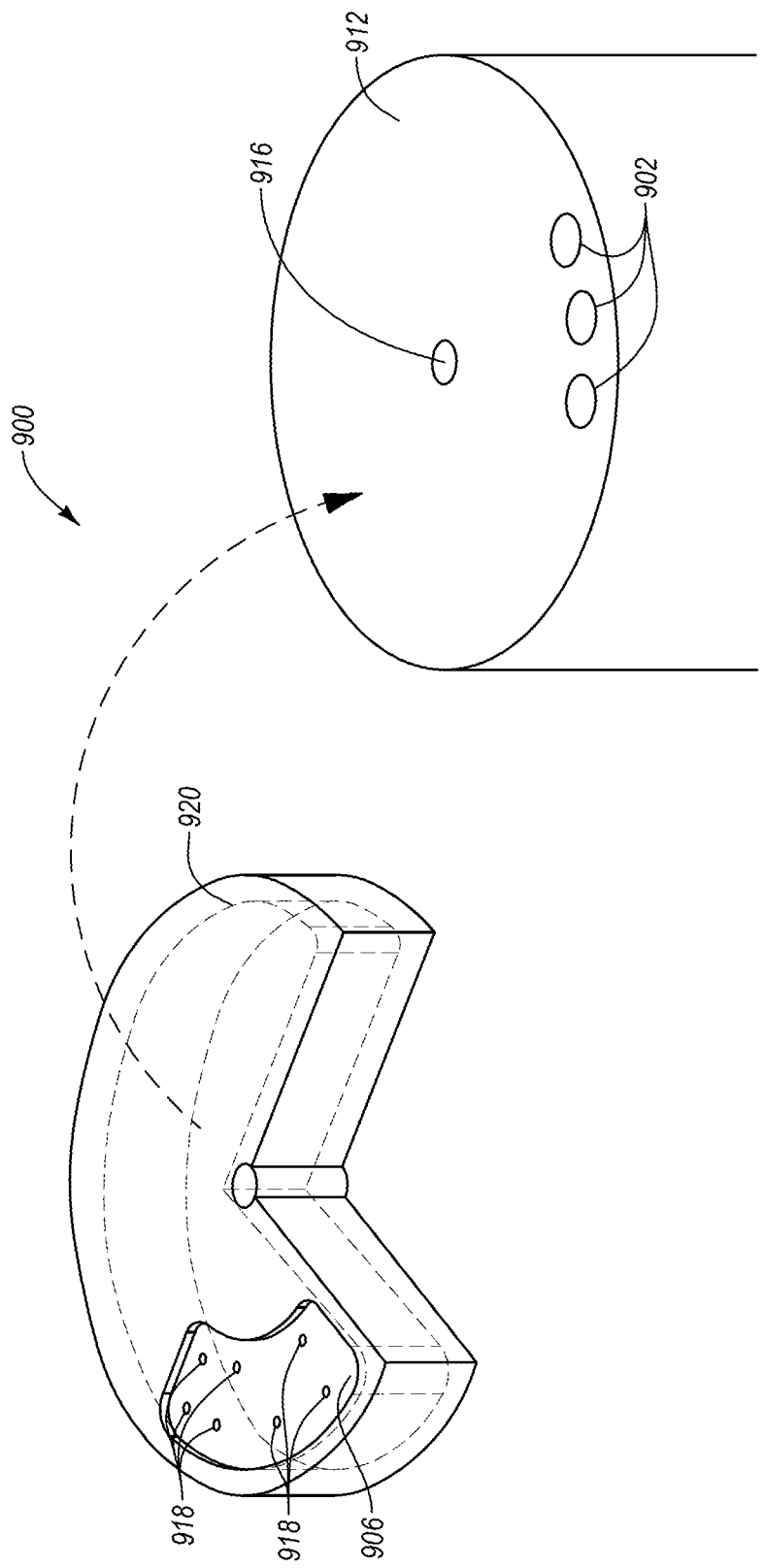
FIG. 9C provides a separated view of portions of the probe illustrated in FIG. 9A.

FIGS. 9A, 9B and 9C (referred to as FIG. 9 herein) depict another illustrative embodiment of a probe with antifouling control. FIG. 9 illustrates a probe 900 with a sensor 902. A body 922 of the probe 900 encloses the sensor 902 and any operating electronics needed to operate the sensor 902. The sensor 902 is exposed on the surface 912.

The body 922 is connected to a portion 904 that is rotatably connected to the body 922. A motor inside the body 922 can be connected to the portion 904 via the engagement shaft 914 to rotate the portion 904 as desired. The motor rotates the shaft 914 that extends from an opening 916 in the body of the probe 900 and thus rotates the portion 904. FIG. 9A, for example, illustrates the probe 900 in an open position. In the open position, the sensor 902 is exposed. In the closed position illustrated in FIG. 9B, the sensor 902 is not exposed and is covered by a wiper 906.

As previously described, the wiper 906 thus covers the sensor 902 when the probe is in the closed position. The portion 904 may also include a chamber 920 that may be filled with biocide. The biocide can dissolve and be delivered to the sensor 902 via the apertures 918.

The portion 904 includes an angle 910. The angle 910 can range from being acute to being obtuse. The angle 910 may be selected such that it does not interfere with the operation of the sensor 902.

The portion 902 can be rotated completely. This ensures that the top surface of the probe can be wiped by the wiper 906. The surface of the portion 904 can be formed from an antifouling material. Also, the sensor 902 is bathed by biocide administered through the apertures 918 when in the closed position.

In one example, a probe with antifouling control includes a first portion having antifouling components and a second portion having antifouling components. The first and second portions are configured to move between an open position and a closed position. This can be achieved by moving the first portion while the second portion remains stationary or vice versa. In addition, the movement of the first portion relative to the second portion or of the second portion relative to the first portion can be, by way of example only, translational or rotational. The probe also includes a sensor to measure an attribute of a fluid (such as water) when the first and second portions are in the open position. When in the open position or the closed position and/or when moving between the open and closed positions, the antifouling components can inhibit fouling of the sensor.

For example, the sensor may be incorporated into the first portion. In this example, the antifouling components of the second portion may include a wiping component that moves across the sensor when the first and second portions move between the open and closed positions. The wiping component may also be configured to wipe or scrape the sensor to remove biological growth or to remove deposits, etc. The antifouling components of the second portion may also include an antifoulant component that delivers an antifoulant at least to the sensor to inhibit fouling. The antifoulant can be delivered to other portions of the probe at the same time or at different times. The antifouling components of the second portion may also include a material component that is located to inhibit fouling as described herein. One of skill in the art can appreciate that the antifouling components can be incorporated into one or both of the first and second portions.

In another example, the probe may include a body. A sensor module may be located or disposed in one end of the body. The probe may also have an antifouling component to inhibit fouling of the sensor component. The antifouling component may include one or more of a material component that forms at least a portion of a first surface of the sensor module and that inhibits fouling of the sensor module, a wiping component arranged to wipe at least a portion of the sensor module, and an antifoulant component configured to deliver an antifoulant to the sensor module or to a portion thereof. The antifouling component may also shutter the sensor module (and in particular the sensor included in the sensor module) to prevent light from reaching the sensor and to eliminate exposure of the sensor and surrounding area in the sensor module to an attachment of biological growth in the closed position.

The embodiments described herein may include the use of a special purpose or general-purpose computer including various computer hardware or software modules, as discussed in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the reader properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modules running on a computing system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A probe with antifouling control, the probe comprising:
   a first portion;
   a second portion, wherein the first portion and the second portion are configured to move between an open position and a closed position;
   a sensor configured to measure an attribute of a fluid when the first portion and the second portion are in the open position, wherein the first portion and the second portion cooperate to cover the sensor in the closed position;
   antifouling components that inhibit fouling of the sensor, wherein the antifouling components include:
      a wiping component, wherein the wiping component moves across the sensor when the first portion and the second portion move between the open position and the closed position; and
      an antifoulant component configured to deliver an antifoulant to the sensor; and
   a feedback component, wherein the feedback component cooperates with at least some of the antifouling components to clean at least a portion of the probe,
   wherein the feedback component includes a controller that measures a current or voltage required to move the first portion and the second portion between the open position and the second position,
   wherein the controller repeatedly moves the first portion and the second portion back and forth two or more times when the current or voltage exceeds a threshold current or threshold voltage such that the wiping component scrubs the portion of the probe.

2. The probe according to claim 1, further comprising a material component to inhibit fouling of at least one of the first portion, the second portion, or the sensor, the material component located on a surface of the second portion and a surface of the first portion, wherein:
   the sensor is incorporated into the first portion; and
   the wiping component and the antifoulant component are incorporated into the second portion.

3. The probe according to claim 2, wherein the second portion is configured to move between the open position where the sensor is exposed to an environment and the closed position where the sensor is covered by the second portion, wherein the antifoulant component bathes the sensor with the antifoulant in the closed position.

4. The probe according to claim 3, wherein the second portion comprises at least one chamber formed therein, wherein the antifoulant component is stored in the at least one chamber and delivered to the sensor via apertures formed in a surface of the second portion that covers the sensor in the closed position, the apertures forming a pathway from the at least one chamber to the surface of the second portion.

5. The probe according to claim 1, wherein the second portion and the first portion cooperate to limit exposure of the sensor to attachment of biological growth when the first portion and the second portion are in the closed position.

6. The probe according to claim 1, wherein at least one of the first portion and the second portion comprises a surface formed, manufactured from or coated with a material that inhibits fouling.

7. The probe according to claim 1, wherein the first portion and the second portion are connected to reduce an amount of light and aquatic life that reaches the sensor when in the closed position.

8. The probe according to claim 1, further comprising a material component located on at least one of the first portion and the second portion, wherein the material component comprises at least one of copper, copper alloy, brass, coin silver, or silver plates or another material that prevents fouling.

9. The probe according to claim 8, wherein the material component inhibits non-biological fouling.

10. The probe according to claim 1, wherein the wiping component comprises a blade and/or scrubber configured to scrape and/or clean at least the sensor, wherein the sensor is substantially flush with a surface of the first portion.

11. The probe according to claim 1, wherein the first portion comprises a groove that engages a tongue on the second portion such that the tongue and groove are slidably engaged allowing the second portion to move between the open position and the closed position and keep the first portion connected to the second portion.

12. The probe according to claim 1, wherein the first portion comprises a shaft that engages the second portion such that the second portion rotates with respect to the first portion allowing the second portion to move between the open position and the closed position.

13. The probe according to claim 1, wherein the sensor includes electronics, further comprising a plurality of seals that protect the electronics from an environment including the fluid.

14. The probe according to claim 1, further comprising a motor and a shaft, wherein the shaft engages with an engagement mechanism formed in the second portion such that rotation of the motor moves the second portion between the open position and the closed position.

15. The probe according to claim 1, wherein the sensor is incorporated into the first portion, wherein:
   a material component that inhibits fouling is located on at least some surfaces of the first portion and the second portion that are not wiped by the wiping component;
   the wiping component is configured to scrub the sensor by repeatedly moving back and forth across the sensor when excessive growth is detected on the sensor;
   the antifoulant component is configured to deliver a biocide or scaling inhibitor to at least one surface of the first portion and to the sensor and to a shaft that moves the portion and the second portion between the open position and the closed position.

16. The probe according to claim 15, wherein the first portion is configured to move between the open position where the sensor is exposed to an environment and the closed position where the sensor is covered by the second portion, wherein the antifoulant component bathes the sensor with a biocide, algaecide, fungicide or scaling inhibitor in the closed position.

17. The probe according to claim 15, wherein the first portion is configured to move between the open position where the sensor is exposed to an environment and the closed position where the sensor is shuttered by the first and second portions, wherein the antifoulant component bathes the sensor with the antifoulant in the closed position.

18. The probe according to claim 15, wherein movement of the first portion and the second portion includes at least one of: translational movement of the first portion or the second portion; or rotational movement of the first portion or the second portion.

19. The probe according to claim 1, wherein movement of the first portion and the second portion flushes foulants from the sensor.

20. The probe according to claim 1, wherein:
the sensor and the antifoulant component are incorporated into the first portion;
the wiping component is incorporated into the second portion; and
a material component is located on a top surface of the second portion and a top surface of the first portion.

21. A probe for measuring an attribute of a fluid, the probe comprising:
a body having a first end and a second end; and
a sensor module disposed in the first end and configured to move at least between an open position and a closed position, the sensor module including a sensor for measuring the attribute of the fluid when the sensor module is in the open position and an antifouling component to inhibit fouling of the sensor module, wherein the antifouling component comprises:
a material component that forms at least a portion of a first surface of the sensor module;
a wiping component connected with a second surface of the sensor module opposite the sensor, wherein the wiping component is arranged to wipe at least a portion of the sensor; and
an antifoulant component configured to deliver an antifoulant to the sensor module,
wherein the sensor module shutters the sensor to prevent light from reaching the sensor and to limit exposure of the sensor and an area surrounding the sensor to an attachment of biological growth in the closed position.

22. The probe according to claim 21, wherein the antifoulant component includes one or more chambers that store the antifoulant, wherein the antifoulant component delivers the antifoulant at least to the sensor via apertures that are adjacent the sensor when in the closed position to bathe the sensor in the antifoulant.

23. The probe according to claim 22, wherein the material component is disposed on a top surface of the sensor module and wherein the material component interfaces with an edge of the body such that the sensor module is disposed inside the body in the closed position.

24. The probe according to claim 22, wherein the sensor module comprises a first portion that includes the sensor and a second portion that includes the wiping component, wherein the second surface is substantially parallel to a third surface that includes the portion of the sensor, wherein the wiping component scrapes the portion of the sensor when the sensor module moves between the open and closed positions and wherein the sensor is bathed in the antifoulant delivered by the antifoulant component when in the closed position.

25. The probe according to claim 24, further comprising a motor and a shaft that translates the second portion laterally to raise and lower the second portion between the open position and the closed position or that rotates the second portion relative to the first portion between the open position and the closed position.

26. The probe according to claim 22, wherein a second antifoulant is integrated into a film on the surfaces or in a reservoir chamber of the sensor module and released over time.

27. The probe according to claim 21, wherein the material component includes at least one of copper, copper alloy, brass, coin silver, or silver plates, or another material that prevents fouling.

28. The probe according to claim 21, further comprising a motor that drives a shaft to move the second portion relative to the first portion to expose the sensor to the fluid for measuring the attribute of the fluid.

29. The probe according to claim 21, further comprising a seal on the first portion that prevents the fluid from entering the body.

30. The probe according to claim 29 wherein electronics are disposed in the body and configured to control the sensor module, the electronics including a feedback component configured to move the wiping component to wipe the sensor repeatedly when the feedback component determines that the sensor is potentially fouled.

31. The probe according to claim 30 wherein the sensor is potentially fouled when a current or a voltage required to move the sensor module between the open position and the closed position exceeds a predetermined current or a predetermined voltage.

32. The probe according to claim 31, wherein the antifoulant component is configured to be refilled with the antifoulant and wherein the material component is removably attached to the sensor module.

33. A probe for measuring an attribute of a fluid, the probe comprising:
a first portion;
a second portion, wherein the first portion and the second portion are configured to move between an open position and a closed position;
a sensor configured to measure an attribute of a fluid when the first portion and the second portion are in the open position;
antifouling components that inhibit fouling of the sensor, wherein the antifouling components include:
a wiping component, wherein the wiping component is placed to move across the sensor when the first portion and the second portion move between the open position and the closed position;
an antifoulant component configured to deliver an antifoulant to the sensor; and
a material component configured to inhibit at least non-biological fouling; and
a feedback component that controls at least one of the antifouling components to clean the sensor when potential fouling is detected,
wherein the feedback component detects potential fouling when a current or a voltage required to move the first portion and the second portion between the open position and the closed position is above a threshold current or a threshold voltage,
wherein the feedback component includes a controller that operates at least one of the antifouling components to clean the sensor when the potential fouling is detected,
wherein the controller moves the wiping component across the sensor multiple times to clean the sensor.

34. The probe according to claim 33, wherein the antifoulant component is configured to bathe the sensor with the antifoulant in the closed position, wherein the first portion and the second portion substantially shutter the sensor from light in the closed position.

35. The probe according to claim 33, wherein the feedback component controls a speed or a pressure with which the controller moves the first portion and the second portion.

* * * * *